United States Patent [19]

Patel et al.

[11] Patent Number: 5,533,992
[45] Date of Patent: Jul. 9, 1996

[54] MATERIAL FOR MEDICAL GRADE PRODUCTS AND PRODUCTS MADE THEREFROM

[76] Inventors: Indrajit Patel, 1115 Riverwood Dr., Algonquin, Ill. 60102; Harold Bowerman, 2240 Shanondale Dr., Libertyville, Ill. 60048; Larry Rosenbaum, 855 Kristin St., Gurnee, Ill. 60031; Rich Mennenoh, 3917 Orleans, McHenry, Ill. 60050; Pat Ryan, 968 Boxwood, Crystal Lake, Ill. 60014

[21] Appl. No.: 828,436

[22] Filed: Jan. 30, 1992

Related U.S. Application Data

[63] Continuation-in-part of Ser. No. 636,337, Dec. 31, 1990, abandoned.

[51] Int. Cl.$^6$ .................................................. A61F 1/00
[52] U.S. Cl. ........................... 604/403; 604/408; 604/282
[58] Field of Search ................................... 128/4, 6, 658; 623/1–3, 12, 3; 604/264, 280, 282, 403, 408, 411, 415, 416

[56] References Cited

U.S. PATENT DOCUMENTS

| | | |
|---|---|---|
| 3,562,352 | 2/1971 | Nyilas . |
| 4,048,254 | 9/1977 | Hillier et al. . |
| 4,331,142 | 5/1982 | Degen . |
| 4,377,010 | 3/1983 | Fydelor et al. . |
| 4,479,795 | 10/1984 | Mustacich et al. . |
| 4,516,977 | 5/1985 | Herbert . |
| 4,623,347 | 11/1986 | Kira . |
| 4,725,355 | 2/1988 | Yamamoto et al. ................. 210/502.1 |
| 4,753,222 | 6/1988 | Morishita ................................. 128/4 |
| 4,810,582 | 3/1989 | Gould et al. . |
| 4,826,945 | 5/1989 | Cohn et al. . |
| 4,834,755 | 5/1992 | Silvestrini et al. ..................... 623/13 |
| 4,915,893 | 4/1990 | Gogolewski et al. .................. 264/205 |
| 4,923,470 | 5/1990 | Dumican ................................ 623/11 |
| 4,996,054 | 2/1991 | Pietsch et al. ............................ 623/1 |
| 5,009,648 | 4/1991 | Aronoff et al. ......................... 604/332 |
| 5,085,649 | 2/1992 | Flynn ..................................... 604/282 |
| 5,156,785 | 10/1992 | Zdrahala ................................ 604/264 |

FOREIGN PATENT DOCUMENTS 56-116467  7/1980  Japan .

*Primary Examiner*—Sam Rimell

[57] ABSTRACT

A non-PVC, non-DEHP material is provided for medical grade products such as tubing and containers. The material comprises a monolayer blend of a polyurethane based material. In an embodiment, the resultant product of the present invention has good low temperature characteristics, is autoclavable, and RF sealable. Accordingly, the resultant product can be utilized for applications which heretofore have been filled in the marketplace by DEHP plasticized PVC products.

32 Claims, 1 Drawing Sheet

MATERIAL FOR MEDICAL GRADE PRODUCTS AND PRODUCTS MADE THEREFROM

RELATED APPLICATIONS

This is a continuation-in-part of U.S. patent application Ser. No. 07/636,337, filed on Dec. 31, 1990, now abandoned.

BACKGROUND OF THE INVENTION

The present invention relates generally to medical products and compositions for making same. More specifically, the present invention relates to non-PVC materials and medical containers, devices, and tubing made therefrom.

Typically, medical tubing, for example for use in blood collection sets as the donor tubing, is constructed from plasticized polyvinyl chloride (PVC). Usually, the PVC is plasticized with DEHP. Likewise, some medical containers and devices are constructed from plasticized polyvinyl chloride.

In one method of constructing such containers, the container is filled through an open-ended filling port. A membrane tube closure is then coated with a solvent such as cyclohexanone and inserted into the fill port tube. During this process, a chemical bond is achieved between the fill port and membrane tube closure.

Recently there has been concern with respect to the use of DEHP plasticized PVC. DEHP has been alleged to be a suspected carcinogen. However, the characteristics that are afforded by plasticized PVC are very desirable especially in the medical area and for uses such as, for example, the donor tube in blood collection systems.

With respect to tubing, for example, it typically must have low temperature characteristics. Furthermore, it is desirable that the tubing can be solvent bonded to a PVC material: the containers to which the tubing is secured are usually constructed from PVC. It is also desirable that the tubing is RF sealable so as to be compatible with blood tubing sealing equipment presently used.

Likewise, medical containers must exhibit certain desirable properties. It is desirable that the container can be sealed, either to itself or other components such as tubing, by conventional sealing methods such as radio frequency, sonic welding, thermal welding, and medical grade solvent bonding systems. The containers must be thermally stable at 121° C. without irradiating or cross-linking for autoclavability. The scrap should be recyclable. The container should withstand low temperatures (−60° C. to −80° C.) and should be compatible with multilayer structures that may not require a tie layer. The container needs to be sufficiently permeable to WVTR to minimize haze during autoclaving. For use as a blood bag, the container must be sufficiently permeable to oxygen and carbon dioxide to store blood components such as platelets and plasma. Additionally, the container should be scuff resistant.

Presently, plasticized (flexible) polyvinyl chloride (PVC) materials are widely used for medical applications, such as medical solution containers (parenteral), storing red cells, plasma, and platelet containers. The desirable properties of the above applications include: extrudability; moldability; flexibility; transparency; resistance to heat; cost; and ability to be sealed using conventional sealing technology, such as radio frequency, heat sealing, sonic welding, thermal sealing, and medical grade solvent system.

Typically, the containers constructed from plasticized PVC are sterilized by autoclaving at 121° C. for 60 minutes or less. Therefore, any material that will be used as a substitute for plasticized PVC must withstand such autoclaving (121° C., 60 minutes).

Polyolefinic containers made from ethylenevinyl acetate have been developed for medical solutions. Containers made from ethylenevinyl acetate (EVA) are not thermally stable at 121° C. Therefore, the film or container needs to be radiated by electron beam process or gamma radiation to achieve autoclavability.

Although there are other components in the art from which, arguably, such medical products could be created, each of these components suffers certain disadvantages. Most importantly, the resultant product does not have the same desirable characteristics as a plasticized PVC product.

For example, flexible polyester is not as RF responsive as is plasticized PVC. Aliphatic polyurethane is not autoclavable. Further, with respect to tubings, tubings created from such materials due to their characteristics cannot be used on currently used commercial machinery in, for example, a blood collection system.

U.S. patent application Ser. No. 07/270,006, filed Nov. 14, 1988, discloses a citrate ester in a non-PVC material. U.S. patent application Ser. No. 07/494,045, filed May 15, 1990, is a divisional application to that patent application. Both of these applications are assigned to the assignee of the present invention.

SUMMARY OF THE INVENTION

The present invention provides a non-PVC and non-DEHP material that can be used for medical products. More particularly, the present invention provides medical products such as containers and tubing made from such material.

To this end, the present invention provides monolayer material comprising an aliphatic based polyurethane alloy that provides the necessary characteristics for use in constructing medical products.

In an embodiment, the present invention provides medical grade tubing. The resultant tubing of the present invention has good low temperature characteristics, and unlike EVA tubing that also performs well at low temperatures, the tubing of the present invention is RF sealable even at low power levels. Therefore, the resultant tubing of the present invention is compatible with blood tubing sealing equipment presently used in the marketplace with plasticized PVC tubing. Additionally, the resultant product is autoclavable. In an embodiment, a medical grade tubing is provided comprising a blend of polyurethane and polyester, the resultant tubing being autoclavable and RF sealable.

The present invention also provides a medical grade tubing comprising a blend of polyurethane, polyester, and butyryl trihexyl citrate.

In an embodiment, a medical grade tubing is provided comprising a blend of approximately 30 to about 40 weight percent polyester and approximately 60 to about 70 weight percent polyurethane.

Additionally, a non-PVC, non-DEHP material is provided for a medical grade tubing comprising approximately 30 to about 50 weight percent polyester and approximately 50 to about 70 weight percent polyurethane. In an embodiment, the material includes a citrate ester such as butyryl trihexyl citrate.

In a further embodiment, an assembly for the collection of blood is provided including a tubing comprising approximately 30 to about 50 weight percent polyester and approximately 50 to about 70 weight percent polyurethane. In an embodiment, the tubing includes a citrate ester. This tubing is autoclavable and RF sealable.

In an embodiment, a medical grade tubing is provided comprising a blend of polypropylene, ethylenevinyl acetate, and polyurethane.

In an embodiment, a medical grade tubing is provided comprising a blend of ethylenevinyl acetate, polyester, and polyurethane.

In an embodiment, a medical grade tubing is provided comprising a blend of polypropylene, styrene ethylene butylene styrene, polyester, and polyurethane.

In an embodiment, the present invention provides medical grade containers for housing solutions or devices. The containers are constructed from aliphatic based polyurethane alloys.

The resultant containers provide the desirable characteristics of plasticized PVC containers without the perceived disadvantages. These characteristics include the ability of the container film to be sealed using conventional sealing methods such as RF sealing, sonic welding, thermal welding, and medical grade solvent bonding systems. The containers are thermally stable at 121° C. without irradiating or cross-linking for autoclavability. The containers can withstand low temperatures (−60° C. to −80° C.). The containers are sufficiently permeable to WVTR to minimize haze during autoclaving. The containers have sufficient permeability to oxygen and carbon dioxide to allow them to store blood components such as platelets and plasma. The containers are scuff resistant.

In an embodiment, the container comprises a monolayer blend of polyurethane and polyester.

In an embodiment, a medical grade container is provided comprising a monolayer blend of polypropylene, ethylenevinyl acetate, and polyurethane.

In an embodiment, a medical grade container is provided comprising a monolayer blend of ethylenevinyl acetate, polyester, and polyurethane.

In an embodiment, a medical grade container is provided comprising a monolayer blend of polypropylene, styrene ethylene butylene styrene, polyester, and polyurethane.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

Non-PVC, non-DEHP materials are provided for medical grade products. The materials comprise monolayer polyurethane based alloys that provide the properties afforded by plasticized PVC. In an embodiment, the material comprises a blend of polyurethane and polyester. The resultant products of the present invention have good low temperature characteristics, are autoclavable, and RF sealable. Accordingly, the resultant products can be utilized for applications which heretofore have been filled in the marketplace by DEHP plasticized PVC products, for example, PVC tubings and containers.

Additionally, the material of the present invention is extrudable, injection moldable, and blow moldable. Because it is a non-PVC, non-DEHP material, it eliminates the environmental concerns of acid rain and the alleged carcinogenic properties of DEHP. Further, with respect to a tubing, the resultant tubing is kink resistant.

In an embodiment, it has also been found that a resultant tubing of the present invention, made from a polyurethane and polyester blend, can be solvent bonded to PVC material that is currently utilized by using cyclohexanone. Additionally, the tubing is RF sealable allowing the tubing to make a donor tubing, or other tubing, that can be sealed on commercial blood collection equipment. Furthermore, the material can be autoclaved either through steam, ETO, or gamma sterilization.

In an embodiment, preferably, the composition for creating the medical grade tubing comprises approximately 30 to about 50 weight percent polyester and approximately 50 to about 70 weight percent polyurethane. It has been found that a polyurethane available from Morton International under the tradename MORTHANE, PE-192-100 functions satisfactorily in the present invention. It has also been found that polyester available from Eastman Chemical Company under the tradename PCCE-9966 functions satisfactorily with the polyurethane available from Morton International.

In an embodiment, the polyester and polyurethane are blended with a citrate ester. The citrate ester improves the flexibility of the resultant product. It has been found that butyryl trihexyl citrate available from Moreflex under the designation CitroFlex B-6 functions satisfactorily in this regard—preferably approximately 5 to about 7.5 weight % citrate is used.

As set forth below, other thermoplastic aliphatic polyurethane based alloys can be used to create medical grade tubing having similar properties to a plasticized PVC tube. These blends include:

1. Polypropylene+ethylenevinyl acetate+polyurethane.
2. Polypropylene+styrene-ethylene-butylene-styrene (Kraton)+polyurethane.
3. Polyester (PCCE)+a thermoplastic copolyester elastomer (Hytrel)+polyurethane.
4. Polypropylene+styrene-ethylene-butylene-styrene (Kraton)+polyester (PCCE)+polyurethane.
5. Ethylenevinyl acetate+PCCE+polyurethane.

Figure 1:
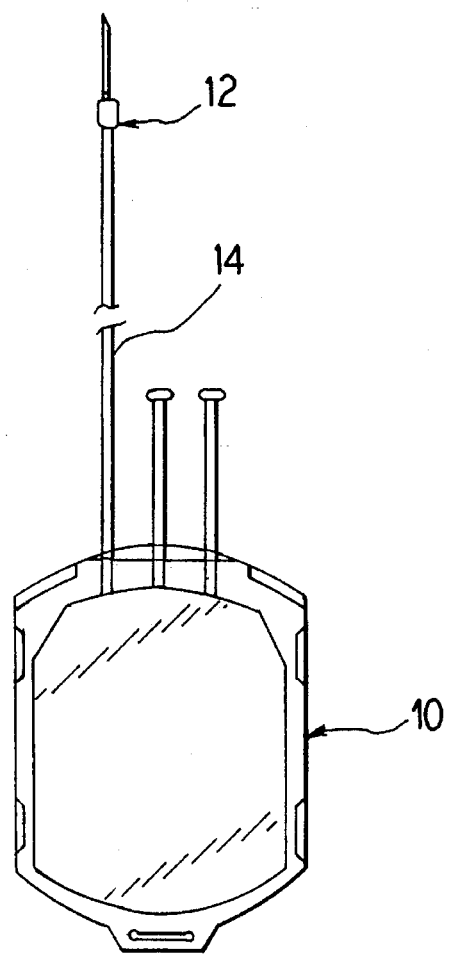
FIG. 1 illustrates a blood collection assembly including an embodiment of a medical grade tubing of the present invention.

FIG. 1 illustrates a blood bag 10 and set 12 including a tubing 14 fabricated from the material of the present invention. In the embodiment, the blood bag 10 is constructed from PVC. However, as set forth below, pursuant to the present invention, the blood bag 10 can be constructed from a non-PVC non-DEHP material.

The tubing 14 of the present invention is constructed from a polyurethane alloy of the present invention that allows the tubing to be solvent bonded to the bag 10. Additionally, the alloy allows the product to be autoclaved. Further, the tubing 14 is RF weldable allowing full use of the commercial blood tube sealing equipment. An example of a blood bag system in which the tubing 14 of the present invention can be used is disclosed in U.S. Pat. No. 4,608,178.

Figure 3:
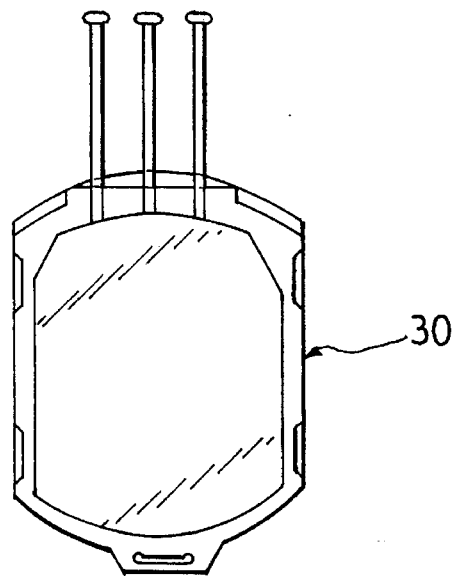
FIG. 3 illustrates a perspective view of a container constructed pursuant to the present invention.

As previously stated, the present invention also provides materials that can create non-PVC, non-DEHP medical grade containers. To this end, in a further embodiment of the present invention, the thermoplastic aliphatic based polyurethane alloys of the present invention can be used to construct a container 30 such as that illustrated in FIG. 3. The container can be used to house a solution or medical device. The blends of the present invention provide containers that enjoy characteristics similar to DEHP plasticized PVC but do not have the perceived disadvantages of DEHP plasticized PVC.

Pursuant to the present invention, the container 30 can be constructed from polyurethane blends such as: polypropylene, ethylenevinyl acetate, and polyurethane; ethylenevinyl acetate, polyester, and polyurethane; polypropylene, styrene ethylenebutylene styrene, polyester, and polyurethane; and polypropylene, styrene-ethylene-butylene-styrene, and polyurethane.

By way of example and not limitation, examples of the present invention will now be set forth.

EXAMPLE 1

Polyester (PCCE) available from Eastman Chemical Company under the designation PCCE-9966 and thermoplastic polyurethane (PE) available from Morton International under the designation PE-192-100 were utilized. Three formulation blends were created. The blends were as follows:

| Designation | PCCE | PE |
|---|---|---|
| 1 | 40% (2 lbs) | 60% (3 lbs) |
| 2 | 35% (1.75 lbs) | 65% (3.25 lbs) |
| 3 | 30% (1.5 lbs) | 70% (3.5 lbs) |

With the above formulations, the total blend of each formulation was 5 pounds. Approximately 0.1% Acrawax was added to each formulation.

Each formulation was weighed and tumble-blended and kept in an oven at 150° for two hours prior to pelletizing a total of 25 pounds of material was tumble-blended per formulation blend.

The blended material was then pelletized. The following conditions were used:

```
a 1½" Killion extruder
24:1 L/D
3:1 C.R.
Screen peek 40/100/200/100/40
Barrel zone #1 340° F.
       zone #2 360° F.
       zone #3 375° F.
Die    zone #1 370° F., melt temp. 380° F.
RPM 50, Amps 15
```

Each formulation was pelletized and saved for extruding tubing.

The pellets of each formulation were dried at 160° F. for two hours. The extrusion conditions were as follows for each of samples 1, 2, and 3:

```
Barrel zone #1 300° F.    RPM 15
       zone #2 330° F.    Amps 11
       zone #3 330° F.    Killion 1½"
Die    zone #1 340° F.    L/D:24:1
       zone #2 340° F.    C.R.:3:1
Melt temp 343° F.         screen peak 40/100/200/100/40
Back pressure 4800–5000 psi
Belt roller 3.8
```

-continued
```
Air pressure w/bleed 3.5 psi for tubing die
Belt roller setting 3.8
Tubing size .118" × .020 WL × 100 FTL
```

The tubing of each formulation was extruded and saved for functional testing. The tubing of formulations 2 and 3 were tacky during coiling.

The tubing of formulation 1 was heat aged at 240° F. for 50 minutes in a circulating air oven. At that temperature and time, the tubing survived without deformation to the tube. This condition was used to simulate an autoclave cycle.

Also, the material was tried on a Hematron, with and without water, to investigate the RF sealability of the tubing. In both cases, the tubing of formulation 1 sealed the same as PVC tubing, using a presently available Hematron heat sealer.

Also the tubing of formulation 1 was tried with the present design of a roller clamp to verify its functionality. The formulation 1 tubing performed the same as did PVC tubing.

The formulation 1 tubing was tested for solvent bondability to itself, a presently used donor port and a commercially available PVC blood bag bushing were used. The tubing was attached using a presently used cyclohexanone solvent system. It was found that the tubing broke before the solvent bonding failed. Also, the formulation 1 tubing was found to be kink resistant.

The formulation 1 tubing was tried for stripping the air from the tubing. The tubing was filled with colored water, sealed using a Hematron and stripped with a tubing stripper. The performance of the tubing was as good as that of PVC tubing.

The clarity of formulation 1 tubing was found to be contact clear: the same as presently used PVC. Clarity can be improved during extrusion processing, for example, by proper orientation of the tubing during inline extrusion process.

The tubing made from formulation 1 was attached to a needle assembly by being frictional fit. The attached tubing and needle assembly was sterilized and tested on an Instron and was found to perform as well as a PVC tubing and needle assembly. The results of the tests are as follows:

| Results | Sample | Pull Force, Tubing to Needle Post |
|---|---|---|
| Tubing | 1 | 20.8 lbs., TBG Broke |
| Formulation | 2 | 20.9 lbs., TBG Broke |
| No. 1 | 3 | 22.6 lbs., TBG Broke |
|  | 4 | 21.6 lbs., TBG Broke |
|  | 5 | 21.1 lbs., TBG Broke |

It should also be noted that if tackiness of the material on coiling is a problem, the increased addition of a small amount of an amide wax such as Acrawax, available from Glyco, can resolve the problem.

The above samples demonstrate that the present invention provides a non-PVC, non-DEHP material that can be made into medical tubing. The material can be RF sealed at low frequency and power, such as on a Hematron dielectric sealer. The resultant tubing is kink resistant and solvent bondable. It has similar functional properties to standard PVC tubes. The tubing is autoclavable, gamma sterilizable, can be radiated by an E beam process, or Eto sterilized. Hot stamping can be achieved using standard hotstamp foil. The tubing is contact clear to clear.

EXAMPLE 2

Formulations including a citrate ester were also created. These formulations were as follows:

| Designation | PCCE | PE | BTHC | Acrawax |
|---|---|---|---|---|
| 4 | 40% | 55% | 5% | |
| 5 | 40% | 54.6% | 5% | 0.4% |
| 6 | 45% | 47.1% | 7.5% | 0.4% |
| 7 | 40% | 54.75% | 5% | 0.25% |
| 8 | 45% | 49.75% | 5% | 0.25% |

All of the above percents are weight percents. PCCE was purchased from Eastman, Polyurethane from Morton International, BTHC (Butyryl Trihexyl Citrate) from Moreflex, and Acrawax from Glyco.

Formula No. 4 was created as follows:

A 20 pound batch was produced by weighing 11 pounds of PE-192-100 (Morthane) available from Morton International, 8 pounds of PCCE-9966 from Eastman, (these weights are dry weights), and one pound of CitroFlex B-6 from Moreflex. The PE was added to a mixer and mixed at low speed ($\leq$1,000 RPM) for five minutes. CitroFlex was added and was also mixed at the low speed. PCCE was then added to the mixture and mixing was continued at a low speed for five minutes.

The resultant mixture was discharged into a polyliner. The mixture was then pelletized into a blend.

Formulations 5–8 were created in this manner except, to improve tackiness Acrawax was added to the mixtures.

The resultant mixtures (4–8) are flexible, have improved tackiness and are RF responsive on a Hematron sealer. These formulations are autoclavable, kink resistant, gamma sterilizable, and solvent bondable using cyclohexane.

Figure 2:
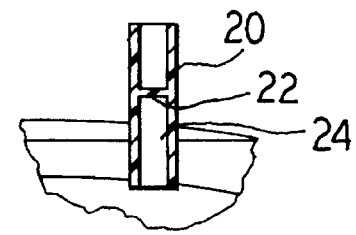
FIG. 2 illustrates a perspective view of a tubing and membrane constructed pursuant to the present invention.

The formulations can be used for creating tubing for a medical container. Also, the formulations can be used for creating a tubing 20 and membrane 22 as illustrated in FIG. 2. The tubing 20 can be created from a formulation such as No. 4 while the membrane 22, that is pierced by a spike to access an interior 24 of the tube is constructed from a formulation such as No. 5.

EXAMPLE 3

A monolayer film and tubing was extruded using an alloy of polypropylene (purchased from Fina)+EVA (purchased from Quantum)+polyurethane (from Morton International). The film was created as follows:

1½" Extruder, Killion. Die Width: 8"
24:1 L/D Ratio. C.R. 3:1
Zone #1 - 340° F.   Zone #3 - 365° F.   Pressure-2000 psi
Zone #2 - 365° F.   Die #1 - 370° F.    RPM: 45
                    Die #2 - 370° F.    AMPS: 4

The resultant film using this alloy was RF sealed at 30% power. An excellent seal resulted. During the testing of RF seal integrity, the film was torn prior to RF seal failure.

EXAMPLE 4

A fusion blend was made using an alloy of EVA (from Quantum)+PCCE (from Eastman Chemical Company)+ polyurethane (from Morton International). The film was created as follows:

1½" Extruder, Killion. Die Width: 8"
24:1 L/D Ratio. C.R. 3:1
Zone #1 - 340° F.   Zone #3 - 365° F.   Pressure-2000 psi
Zone #2 - 365° F.   Die #1 - 370° F.    RPM: 45
                    Die #2 - 370° F.    AMPS: 4

The film was pressed and a Hematron Sealer was used to create a RF seal. During RF sealing, a RF response was noted.

EXAMPLE 5

A monolayer tubing was extruded using polypropylene (from Fina)+styrene-ethylene-butylene-styrene (from Shell)+PCCE (from Eastman Chemical Company)+ polyurethane (from Morton International) pellets. The tubing was made as follows:

1½" Extruder, Killion. Die Width: 8"
24:1 L/D Ratio. C.R. 3:1
Zone #1 - 340° F.   Zone #3 - 365° F.   Pressure-2000 psi
Zone #2 - 365° F.   Die #1 - 370° F.    RPM: 45
                    Die #2 - 370° F.    AMPS: 4

During RF sealing on a Hematron Sealer an excellent seal was achieved.

EXAMPLE 6

The following alloys, constructed as set forth in the above examples, were created and tested. The blends were found to provide the following desired properties:

| Alloys I.D. | Flexibility | Clarity | RF Response | Autoclavability w/o cross link | Low Temperature | Solvent Bonding (Cyclohex) |
|---|---|---|---|---|---|---|
| PP + Kraton | F | P | P | G | G | P |
| PP + Kraton + EVA | G | P | P | G | G | P |
| PP + Kraton + EVA + Hytrel | G | P | P | G | G | G |
| PCCE + Polyurethane Aliphatic or Aromatic, Ali- | G | G | G | G | G | *G |

-continued

| Alloys I.D. | Flexibility | Clarity | RF Response | Autoclavability w/o cross link | Low Temperature | Solvent Bonding (Cyclohex) |
|---|---|---|---|---|---|---|
| phatic is preferred | | | | | | |
| PP + EVA + PU | G | G | G | G | G | F |
| PCCE + EVA + PU | G | G | G | G | G | F |
| PP + Kraton + PCCE + PU | G | F | G | G | G | F |
| PP + Kraton + PU | G | F | F | G | G | *G |
| PCCE + Hytrel + PU | G | G | G | G | G | G |

Key:
P = Poor F = Fair G = Good
PP = Polypropylene
EVA = Ethylenevinyl Acetate (18%–40% VA Content)
PCCE = Copolyester
Kraton = Styrene Ethylene Butylene Styrene
PU = Polyurethane
* = Solvent Bond to Itself and Plasticized PVC These results demonstrate the advantageous characteristics achieved with the polyurethane based alloys of the present invention as compared to alloys without polyurethane.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim as my invention:

1. A medical grade tubing comprising a blend of a thermoplastic polyurethane blend and polyester that is extruded to create the medical grade tubing, the medical grade tubing being autoclavable and RF sealable, the thermoplastic polyurethane blend being chosen from the group consisting of: polypropylene, ethylene vinyl acetate, and polyurethane;polypropylene, styrene-ethylene-butylene-styrene, and polyurethane; polyester, a thermoplastic copolyester elastomer, and polyurethane; polypropylene, styrene-ethylene-butylene-styrene, polyester, and polyurethane: and ethylenevinyl acetate, polyester, and polyurethane.

2. The medical grade tubing of claim 1 comprising approximately 30 weight percent polyester and approximately 70 weight percent polyurethane.

3. The medical grade tubing of claim 1 comprising approximately 35 weight percent polyester and approximately 65 weight percent polyurethane.

4. The medical grade tubing of claim 1 comprising approximately 40 weight percent polyester and approximately 60 weight percent polyurethane.

5. The medical grade tubing of claim 1 including an amide wax.

6. A medical grade tubing comprising approximately 30 to 50 weight percent polyester and approximately 50 to 70 weight percent thermoplastic polyurethane blend, the polyester and the thermoplastic polyurethane being extruded to form the medical grade tubing, the thermoplastic polyurethane blend being chosen from the group consisting of: polypropylene, ethylene vinyl acetate, and polyurethane; polypropylene, styrene-ethylene-butylene-styrene, and polyurethane; polyester, a thermoplastic copolyester elastomer, and polyurethane; polypropylene, styrene-ethylene-butylene-styrene, polyester, and polyurethane; and ethylenevinyl acetate, polyester, and polyurethane.

7. The medical grade tubing of claim 6 including an amide wax.

8. The medical grade tubing of claim 6 wherein the tubing comprises approximately 40 weight percent polyester and approximately 60 weight percent thermoplastic polyurethane.

9. An assembly for the collection of blood including a tubing comprising approximately 30 to about 50 weight percent polyester and approximately 50 to about 70 weight percent a thermoplastic polyurethane blend that is extruded to create the tubing, the tubing being autoclavable and RF sealable, the thermoplastic polyurethane blend being chosen from the group consisting of: polypropylene, ethylene vinyl acetate, and polyurethane;polypropylene, styrene-ethylene-butylene-styrene, and polyurethane; polyester, a thermoplastic copolyester elastomer, and polyurethane;polypropylene, styrene-ethylene-butylene-styrene, polyester, and polyurethane; and ethylenevinyl acetate, polyester, and polyurethane.

10. The assembly of claim 9 wherein the tubing comprises approximately 40 percent polyester and approximately 60 percent polyurethane.

11. The assembly of claim 9 wherein the tubing includes an amide wax.

12. A non-PVC non-DEHP material for medical grade tubing comprising approximately 30 to about 50 weight percent of a thermoplastic polyester blend chosen from the group consisting of: polypropylene, ethylene vinyl acetate, and polyurethane;polypropylene, styrene-ethylene-butylene-styrene, and polyurethane; polyester, a thermoplastic copolyester elastomer, and polyurethane; polypropylene, styrene-ethylene-butylene-styrene, polyester, and polyurethane; and ethylenevinyl acetate, polyester, and polyurethane.

13. The non-PVC, non-DEHP material of claim 12 comprising approximately 40 weight percent polyester and 60 weight percent polyurethane blend.

14. The non-PVC, non-DEHP material of claim 12 comprising approximately 35 weight percent polyester and 65 weight percent polyurethane blend.

15. The non-PVC, non-DEHP material of claim 12 comprising approximately 30 weight percent polyester and approximately 70 weight percent polyurethane blend.

16. The non-PVC, non-DEHP material of claim 12 including an amide wax.

17. A medical grade tubing comprising approximately 30 to 50 weight percent polyester, approximately 50 to 70 weight percent polyurethane, and approximately 5 to about 7.5 weight percent citrate ester.

18. The medical grade tubing of claim 17 including an amide wax.

19. The medical grade tubing of claim 17 wherein the tubing comprises approximately 40 weight percent polyester, approximately 55 weight percent polyurethane, and approximately 5 weight percent citrate ester.

20. The medical grade tubing of claim 17 wherein the citrate ester is butryl trihexyl citrate.

21. An assembly for the collection of blood including a tubing comprising approximately 30 to about 45 weight percent polyester, approximately 50 to about 70 weight percent polyurethane, and approximately 5 to about 7.5 weight percent citrate ester, the tubing being autoclavable and RF sealable.

22. The assembly of claim 21 wherein the tubing comprises approximately 40 percent polyester, approximately 55 percent polyurethane, and approximately 5 weight percent citrate ester.

23. The assembly of claim 21 wherein the tubing includes an amide wax.

24. A non-PVC, non-DEHP material for medical grade tubing comprising approximately 30 to about 45 weight percent polyester, approximately 50 to about 70 weight percent polyurethane, and approximately 5 to about 7.5 weight percent citrate ester.

25. The non-PVC, non-DEHP material of claim 24 comprising approximately 40 weight percent polyester, approximately 55 weight percent polyurethane, and approximately 5 weight percent citrate ester.

26. The non-PVC, non-DEHP material of claim 24 comprising approximately 45 weight percent polyester and approximately 47 to about 50 weight percent polyurethane.

27. The non-PVC, non-DEHP material of claim 25 wherein the citrate ester is butryl trihexyl citrate.

28. The non-PVC, non-DEHP material of claim 25 including an amide wax.

29. A medical grade tubing comprising a monolayer blend of a thermoplastic polyurethane blend chosen from the group consisting of: polypropylene, ethylene vinyl acetate, and polyurethane;polypropylene, styrene-ethylene-butylene-styrene, and polyurethane; polyester, a thermoplastic copolyester elastomer, and polyurethane;polypropylene, styrene-ethylene-butylene-styrene, polyester, and polyurethane; and ethylenevinyl acetate, polyester, and polyurethane.

30. A non-PVC, non-DEHP material for making medical grade products comprising a monolayer blend of a polyurethane based material, the material including a thermoplastic polyurethane blend, the thermoplastic polyurethane blend being chosen from the group consisting of: polypropylene, ethylene vinyl acetate, and polyurethane; polypropylene, styrene-ethylene-butylene-styrene, and polyurethane; polyester, a thermoplastic copolyester elastomer, and polyurethane; polypropylene, styrene-ethylene-butylene-styrene, polyester, and polyurethane; and ethylenevinyl acetate, polyester, and polyurethane, the monolayer blend of the polyurethane based material being extruded to form a medical grade product.

31. A medical container constructed from a monolayer blend of a polyurethane based material, the material including a thermoplastic polyurethane blend, the thermoplastic polyurethane blend being chosen from the group consisting of: polypropylene, ethylene vinyl acetate, and polyurethane;polypropylene, styrene-ethylene-butylene-styrene, and polyurethane; polyester, a thermoplastic copolyester elastomer, and polyurethane;polypropylene, styrene-ethylene-butylene-styrene, polyester, and polyurethane; and ethylenevinyl acetate, polyester, and polyurethane, the monolayer blend of the polyurethane based material being extruded to form a medical container.

32. The medical container of claim 31 wherein said container is used to contain blood components.

* * * * *